(12) United States Patent
Weibel (10) Patent No.: US 7,993,674 B2
(45) Date of Patent: Aug. 9, 2011

(54) DRUG DOSE-FORM AND METHOD OF MANUFACTURE

(76) Inventor: Michael K. Weibel, West Redding, CT (US)

( * ) Notice: Subject to any disclaimer, the term of this patent is extended or adjusted under 35 U.S.C. 154(b) by 640 days.

(21) Appl. No.: 10/366,165

(22) Filed: Feb. 13, 2003

(65) Prior Publication Data
US 2003/0224044 A1 Dec. 4, 2003

Related U.S. Application Data

(60) Provisional application No. 60/356,384, filed on Feb. 13, 2002.

(51) Int. Cl.
*A61K 9/20* (2006.01)
*B29C 67/00* (2006.01)
*B29D 7/00* (2006.01)

(52) U.S. Cl. .......... 424/465; 264/492; 264/212

(58) Field of Classification Search .......... 424/425
See application file for complete search history.

(56) References Cited

U.S. PATENT DOCUMENTS

| | | | |
|---|---|---|---|
| 2,816,666 A | 12/1957 | Nadel | |
| 3,054,503 A | 9/1962 | Hartman, Jr. et al. | |
| 3,503,493 A | 3/1970 | Nagy | |
| 4,136,145 A | 1/1979 | Fuchs et al. | |
| 4,158,411 A | 6/1979 | Hall et al. | |
| 4,305,502 A | 12/1981 | Gregory et al. | |
| 4,371,516 A | 2/1983 | Gregory et al. | |
| 4,552,751 A * | 11/1985 | Inaba et al. | 424/449 |
| 4,574,954 A | 3/1986 | Reid | |
| 4,713,239 A | 12/1987 | Babaian et al. | |
| 5,009,894 A | 4/1991 | Hsiao | |
| 5,046,618 A | 9/1991 | Wood | |
| 5,229,164 A | 7/1993 | Pins et al. | |
| 5,343,672 A | 9/1994 | Kearney et al. | |
| 5,458,879 A | 10/1995 | Singh et al. | |
| 5,486,390 A | 1/1996 | Burns et al. | |
| 5,516,530 A | 5/1996 | Lo et al. | |

(Continued)

FOREIGN PATENT DOCUMENTS

EP 0651997 B1 10/1998

(Continued)

OTHER PUBLICATIONS

The Refractance Window™ Drying Concept : A scientific material explaining the types of refractance window drying concept.*

*Primary Examiner* — Michael G Hartley
*Assistant Examiner* — Nabila Ebrahim
(74) *Attorney, Agent, or Firm* — Patrick J. Hagan; Dann, Dorfman, Herrell and Skillman, P.C.

(57) ABSTRACT

Disclosed is a novel solid dosage unit, preferably in the form of a film or thin troche, containing at least one pharmaceutical agent, and its method of manufacture, which involves introduction of a fluid containing at least one non-volatile material, such as a polymeric film forming substance, a volatile carrier and at least one pharmaceutical agent into a depression or cavity comprising the major element of the packaging film for the finished dosage unit (s), and removing the volatile carrier from the cavity by exposure to radiant energy, whereby the remaining non-volatile residue comprises the desired dosage unit. The packaging film can be subsequently lidded by conventional sealing methods to produce packaged dosage units which are suitable for sublingual and other oral applications.

17 Claims, 2 Drawing Sheets

U.S. PATENT DOCUMENTS

| | | | |
|---|---|---|---|
| 5,631,023 A | 5/1997 | Kearney et al. | |
| 5,648,093 A | 7/1997 | Gole et al. | |
| 5,729,958 A | 3/1998 | Kearney et al. | |
| 5,738,875 A | 4/1998 | Yarwood et al. | |
| 5,763,476 A | 6/1998 | Delbressine et al. | |
| 5,820,820 A * | 10/1998 | Pierce | 422/22 |
| 5,837,287 A | 11/1998 | Yarwood et al. | |
| 5,853,758 A | 12/1998 | Lo | |
| 5,866,163 A | 2/1999 | Myers et al. | |
| 6,083,531 A | 7/2000 | Humbert-Droz et al. | |
| 6,155,423 A | 12/2000 | Katzner et al. | |
| 6,193,999 B1 * | 2/2001 | Gennadios | 424/456 |
| 6,482,516 B1 * | 11/2002 | Sadek et al. | 428/402.24 |
| 7,101,567 B1 | 9/2006 | Sano et al. | |
| 2002/0184969 A1 * | 12/2002 | Kodas et al. | 75/330 |
| 2003/0107149 A1 * | 6/2003 | Yang et al. | 264/134 |
| 2006/0073188 A1 | 4/2006 | Goutay et al. | |

FOREIGN PATENT DOCUMENTS

| | | | |
|---|---|---|---|
| GB | 2111423 A * | 7/1983 | |
| WO | WO 95/20377 | 8/1995 | |
| WO | WO 95/34290 | 12/1995 | |
| WO | WO 97/38679 | 10/1997 | |
| WO | WO 01/12161 | 2/2001 | |

* cited by examiner

FIGURE 1

Top view: empty strip with hollow wells

Side view

FIGURE 2

DRUG DOSE-FORM AND METHOD OF MANUFACTURE

CROSS-REFERENCE TO RELATED APPLICATIONS

This application claims the benefit of U.S. Provisional Application No. 60/356,384 filed Feb. 13, 2002. The entire disclosures of the above-identified provisional application is incorporated by reference herein.

FIELD OF THE INVENTION

This invention relates to the field of manufacturing and dispensing pharmaceuticals. More specifically, methods for producing individually-packaged thin dosage units, such as films and troches, formed in situ are provided. Also provided are methods for producing multi-layer solid dosage units.

BACKGROUND OF THE INVENTION

Several patents are referenced in this application in order to more fully describe the state of the art to which this invention pertains. The disclosure of each of these patents is incorporated by reference herein.

Criteria related to drug mechanism of action, concentration, onset and duration of activity, target tissue selectivity and in vivo stability are important factors in selecting a specific method for drug delivery.

There are six principal routes for drug delivery. Oral delivery is the most common and utilizes unit doses in the form of tablets, capsules, syrups and the like for ingestion and ultimate transport across the gastrointestinal mucosa into systemic distribution. Troches are employed for buccal absorption in the oral cavity and to a lesser extent sublingual application. Atomization for inhalation and absorption by nasal or bronchial membranes has found substantial application for rapid absorption of selected medications. Topical or transdermal adsorption is a preferred method for extended release drug delivery amounting to many hours or several days. Rectal administration by means of suppositories is a further method for drug absorption. Finally, intramuscular injection and intravenous delivery, while invasive techniques, may be the only available options for the medication of interest.

Of the commonly employed drug delivery methods, sublingual delivery probably has the fewest applications of all contemporary methods despite a significant number of advantages. Firstly, the sublingual cavity is highly vascularized. Specifically, the sublingual cavity contains arterial and venous networks embedded in the base of the anterior oral cavity under the tongue in addition to the lingual artery and venae comitante embedded in the underside of the tongue. This vascularization complex communicates directly with the internal jugular vein. Therefore drug absorption in this region bypasses the liver on the first circulation. The advantage of this bypass is that the liver is the principal drug dissipating organ and is largely responsible for the depletion of systemically circulating drugs. Secondly, the sublingual cavity is a catabolically benign region with few, if any, drug degrading chemistries operating within the protected cavity. This is in stark contrast to orally ingested medications which are subjected to degradative environments associated with the gastrointestinal tract. Thirdly, in contrast to the buccal region there is only a thin epithelial barrier to drug transport across the mucosal lining. Finally, the sublingual cavity contains no known flavor sensory organelles which is important as many drugs exhibit a bitter characteristic on exposure to the dorsal papilla of the tongue.

In spite of its theoretical appeal, however, the sublingual route of administration has not found widespread use as the method of choice for drug delivery. The best known application is administration of nitroglycerin in a rapidly disintegrating dosage for treatment of angina pectoris. Nitroglycerin is rapidly transported across the sublingual mucosa giving immediate relief via ultimate communication with the internal jugular vein.

There are probably several factors operating collectively to create a bias against sublingual administration of drugs. Firstly, the sublingual cavity is readily stimulated to activate the sublingual gland to produce saliva in order to rinse the cavity. This can result in dilution and transport of the drug into the back of the oral cavity ultimately entering the esophageal tract and the stomach. Secondly, there are attendant taste consequences of release from the sublingual cavity and dissemination of the drug of interest into other areas of the oral cavity. Finally, sublingual administration of drugs delivered in tablet or capsule form is uncomfortable relative to ingestion.

Pharmaceutical agents to be delivered as an individual dose in tablet and capsule form are easy to manufacture. They are commonly packaged as a loose count in vials, jars, or bottles. Alternatively, they may be dispensed from thermoformed blister packs, which are continuously produced from a roll stock, packaging film matrix. The film is heated to its thermoplastic temperature and subjected to an automated die molding process to produce an array of indented wells or depressions projecting from the plane of the film. After indentation of the film, preformed dose forms such as tablets and capsules are flooded across the indented film surface to saturate the well sites. The excess tablets or capsules are removed from the flooded area and the loaded blister array is lidded by the application of a heat sealable web closure. The line or array of unit packaged dose forms is typically segmented into a cluster of contiguous units for final packaging thereby forming a blister pack. The blister pack can be subsequently perforated along a tear line to allow for easy removal of individual, unopened doses from the main body of the blister pack cluster.

A variation of this conventional thermoform, fill and seal process for preformed pharmaceutical dosage units is the use of the technique to produce dosage units that are formed in situ by lyophilization. See, for example, U.S. Pat. Nos. 4,305,502 and 5,729,958.

There are several advantages to unitized compartmentalization of a preformed, individual dose form versus multi-unit bulk packaging. Firstly, the environment of the contained dose form can be controlled. Many drugs in conventional dose form are susceptible to oxidation, photolysis, or hydrolysis. Appropriate design or selection of the encapsulating package matrix can relieve these problems. Secondly, unit containment offers the convenience of carrying one or two individual doses unobtrusively without the possibility of microbial, chemical, or physical contamination.

Dosage units in thin form, such as films or troches, on the other hand, are difficult to manufacture, particularly those with an unusual shape. Additionally, the indexing and packaging is more complex. Continuous cast films containing active substances derived from water soluble or dispersible matrices typically require the added complication of casting onto a sacrificial support film to achieve sufficient strength for collection and converting. As an example, a viscous polymeric fluid containing the drug of interest is extruded onto a continuous advancing belt which moves into a thermally elevated environment. Typically the belt is heated by conduction from the bottom with steam and the exposed surface of the film is subjected to a heated, forced air stream. The dried continuous cast film, with or without backing film, is removed from the belt and collected as roll stock. The roll stock is delaminated if a support film was employed and converted by standard die cutting methods or other segmentation processing into individual dosage forms. The dosage forms are then indexed and packaged into a loose fill dispenser. Film-like dosage forms produced by this approach, in contrast to tablets or capsules, are extremely difficult to count, index, and transfer into a convenient multidose package form that allows for the delivery of a single dose without compromise of the packaging integrity of the remaining units. A dosage unit that could be economically produced in the form of a thin film or troche with individualized packaging for each dose would alleviate these difficulties.

SUMMARY OF THE INVENTION

In accordance with the present invention, there is provided a novel pharmaceutical dosage unit in the form of an orally administrable solid, preferably a film, and a method for its concomitant formation and unit packaging.

In a particular embodiment, the method of the invention combines thin film technology with form/fill/seal processing. Specifically, the method involves providing a sheet having at least one depression of desired shape therein, a flowable composition comprising at least one systemically active pharmaceutical agent, a non-volatile matrix material and a volatile carrier medium. The method then involves depositing the composition in at least one depression and subjecting the deposited composition to electromagnetic (radiant) energy sufficient to volatilize the carrier medium without compromising the physical and chemical properties of the packaging matrix. The exposure to radiant energy yields the desired solid dosage unit comprising the non-volatile material and one or more pharmaceutical agents, which dosage unit has an outside configuration conforming to the inside configuration of the depression. The method can also comprise affixing a lidding sheet to the blister pack sheet to seal the dosage unit-containing depression(s).

In accordance with another aspect of the invention, a method of producing a multi-layer solid dosage unit is provided. This method comprises synthesizing a desired solid dosage unit comprising a nonvolatile material and one or more pharmaceutical agents as described herein and depositing a second composition within the depression(s) of the blister pack sheet and re-exposing the unit to radiant energy. The method can also comprise affixing a lidding sheet to the dose containing sheet.

DETAILED DESCRIPTION OF THE INVENTION

As mentioned above, a major obstacle to the development of a sublingual dosage form is the cost effective production and packaging of film-like structures. Another consideration is the ability to produce a geometrical configuration which optimizes the coverage of the absorptive mucosal surfaces under the tongue thereby enhancing the localization of the drug to the intended delivery site. Dosage form configurations which deviate from square or rectangular swatches are difficult to manipulate after conversion from the roll stock and incur substantial yield losses in the conversion step from roll stock to individual dosage units due to the generation of scrap. Further, multiple layered films, which are highly desirable, are simply not feasible without coextrusion, sequential casting and drying, or sophisticated lamination.

It has now been discovered that a shallow-well blister pack can serve as a platform for concomitant in situ dose form construction and packaging by use of controlled application of electromagnetic (radiant) energy to solidify the contents of each individual well. The method consists of filling a well with a drug-containing fluid film matrix which is then solidified in situ, resulting in a solid dosage form in the well. More preferably, a flowable composition of a volatile, continuous liquid phase containing one or more dissolved substances and/or one or more dispersed phase substances is added to a preformed well or depression in the packaging material. The non-volatile component(s) containing the pharmaceutical agent are solidified in the depression by controlled application of radiant energy, such as infrared and/or microwave radiation to remove the solvent or volatile continuous phase. The wavelength and intensity of radiant energy is selected to promote preferential absorption of the radiation by the fluid in the well without compromising the packaging matrix, thereby promoting solidification of the well contents. A notable advantage of the method of the invention is that the pharmaceutical dosage unit is generated simultaneously with its introduction into the packaging material. Therefore doseform converting, indexing and packaging is reduced to a single step.

Additionally, the instant invention allows for a multiplicity of film layers to be readily achieved as each subsequent filling and reduction to a contiguous overlaying layer can be generated at a separate filling/drying station spaced apart from the previous stage. The ability to provide a multi-layered film as a dosage form is important in sublingual application. In order to localize the active drug component onto the sublingual mucosa and maintain it in close contact for diffusion into the target vascularized tissue area, it may be desirable to have an outer layer with reduced solubility. This would protect or restrict discharge of an inner layer containing the pharmaceutically active component into the salivary flow and thereby inhibit its exiting the sublingual cavity.

The packaged dosage unit of the present invention allows convenient dosing of a wide variety of pharmaceutical agents including, but not limited to, the following agents alone or in combination: an analgesic agent, anti-inflammatory agent, anti-bacterial agent, anti-viral agent, anti-fungal agent, antiparasitic agent, tumoricidal or anti-cancer agent, protein, hormone, neurotransmitter, peptide, glycoprotein, immunoglobulin, immunomodulator, polysaccharide and local aesthetic.

The novel dosage units of the invention may also include various excipients or processing aids, including, without limitation, lubricants, disintegrates, plasticizers, binders, absorbents, diluents, or the like, as needed or desired, in accordance with established pharmaceutical industry practice.

Substances intended for use, singly or in combination, as the film-forming matrix include, but are not limited to: water-soluble or dispersible hydrocolloidal gums such as gum arabic, xanthan gum, guar gum, pectin, alginates, carrageenan, pullulan, curdlan, β-glucans, dextrans and gum tara; hydrolytically or chemically modified oligosaccharides and polysaccharides such as chitosan, low dextrose equivalent (DE) starches, maltodextrins, polydextrose, high amylose starch, lipophilic substituted starches, pregelatinized starches, and propylene glycol alginate; water-soluble cellulose ethers such as hydroxypropyl cellulose, sodium carboxymethylcellulose, hydroxypropyl methylcellulose, methylcellulose and ethylcellulose; water-soluble synthetic polymers such as polyvinyl pyrrolidone, polyethylene glycols, and polylactic acid; soluble or dispersible proteins such as gelatin, prolamines (zein, gluten), whey protein isolates, casein and salts thereof, soy protein isolates, and albumens; and low molecular weight carbohydrates such as maltose, maltitol, mannitol, sorbitol, erythritol, dextrose, sucrose, lactose and lactitol. The above are provided as exemplary ingredients and are not intended to limit the compositional scope of the film-forming matrix.

Figure 1:
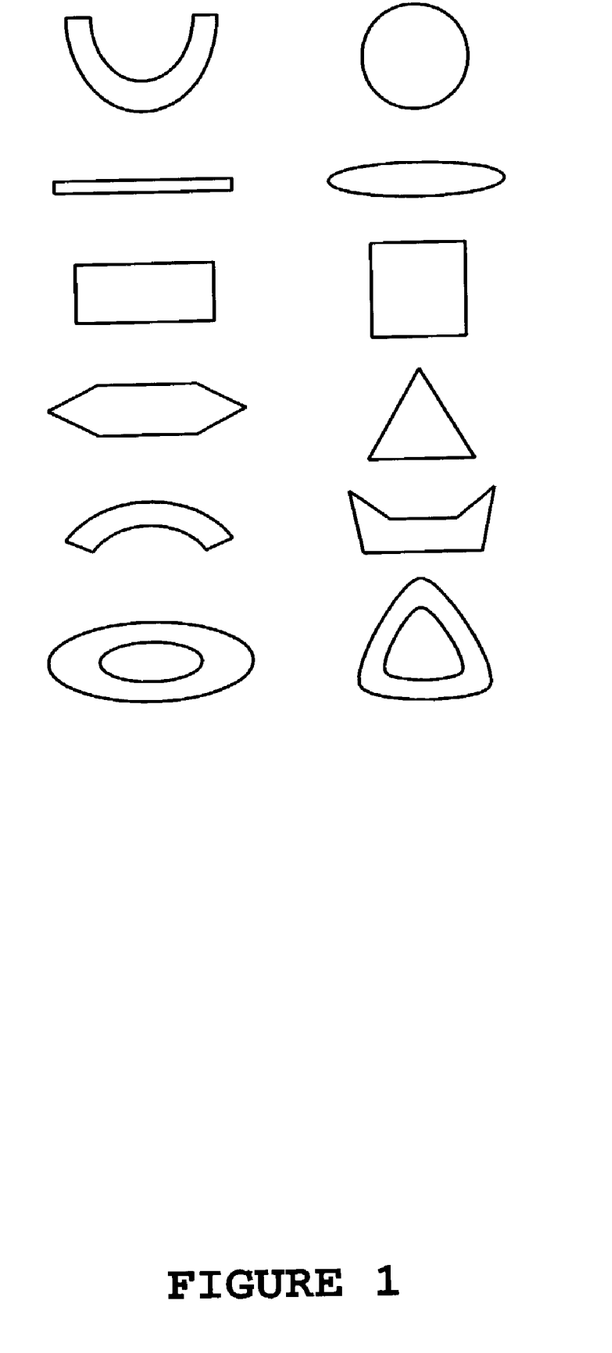
FIG. 1 is a schematic drawing of various shapes of depressions within the blister packs and subsequently formed dosage units.

The dosage unit can assume a number of different configurations, depending on the inside configuration of the well or depression in which it is formed. These configurations may vary in longitudinal cross-section, ranging from closed curve shapes such as circular or elliptical, to polygonal shapes, which may be regular or irregular, including, but not limited to: a triangle, rectangle, square, rhombus, pentagon, hexagon, a hybrid of such geometric shapes or a fragment of such geometric shapes (see FIG. 1).

The shape of the resultant dosage unit may be adapted to optionally adhere to a specific target surface in the oral cavity such as the ventral area of the tongue for localized transport of the active drug into a specific vascularized area.

It is also possible to provide multi-layer dosage units in accordance with this invention having a slowly dissolving layer on the outer surface exposed to salivary discharge. This provides a comfortable and compliant platform for drug delivery. Ultimately the matrix material of the dosage unit would dissolve during the process of releasing the drug and enter the gastrointestinal system.

The opportunities for sublingual dosage form administration are substantial. A number of situations arise where immediate administration and response to a drug are desired. Sublingual administration may be possible for selected analgesic medications. A case in point is the administration of medication for acute pain. Aside from systemic injection there are few fast-acting oral drugs for intense pain, and many in tablet form have the undesirable side effects of nausea and vomiting. Further, oral ingestion and swallowing may be difficult for certain groups of patients.

Another application is alleviating motion sickness or nausea. Oral remedies are ineffective as after ingestion they seldom are retained in the gastric region for a sufficient time to initiate systemic distribution due to regurgitation. Sublingual administration avoids this problem.

Another potential utility is the sublingual administration of drugs for control of type II diabetes. Such drugs are typically taken orally by diabetics 1-2 hours before a meal for postprandial control of their blood sugar. The ability to administer a sublingual dose immediately after or concomitant with a meal would be desirable for situations where it is either inconvenient to take the medication before eating or the individual simply forgot to do so.

Another application would be sublingual application of anti-anxiety medication for control and response of phobia induced anxiety such as agoraphobia, acrophobia, or claustrophobia. Anti-anxiety medications include, but are not limited to: Xanax® (alprazolam; Pharmacia, Peapack, N.J.), Effexor® (venlafaxine HCl; Wyeth, Madison, N.J.), and Paxil® (paroxetine HCl; London, United Kingdom).

A wide range of materials are currently available for use as the thermoformable, plastic packaging material of the instant invention including, but not limited to: polyvinyl chloride, styrene polymers, polymethyl methacrylate, polycarbonate, polyphenyl ether, cellulose derivatives, polyamides, polysulfones, high and low density polyethylenes, polypropylene, polyalkylene terephthalates, and polyphenylene sulfides. Two types of thermoformable plastic packaging materials were used in the examples provided hereinbelow. A lower range temperature film (EASTAR®) of noncrystalline polyethylene terephthalate (PETG) that was used for thermoforming was a proprietary film supplied by Eastman Kodak (Kingsport, Tenn.). The higher range temperature film employed was a proprietary three layer coextruded film (TOPAS®) comprised of polypropylene/cyclic olefin copolymer/polypropylene (PP/COC/PP) supplied by Ticona (division of Celanese AG, Summit, N.J.). Because the PP/COC/PP film is a relatively high temperature film for blister pack thermoforming, it is more forgiving with respect to in situ thermal excursion within the dose form well and less control of radiant energy intensity is required. Conversely, the lower temperature thermoformable PETG film matrix requires more care and control of the radiant energy intensity, but is still compatible with both radiant energy induced, in situ evaporation methods, as demonstrated in the provided examples.

Figure 2:
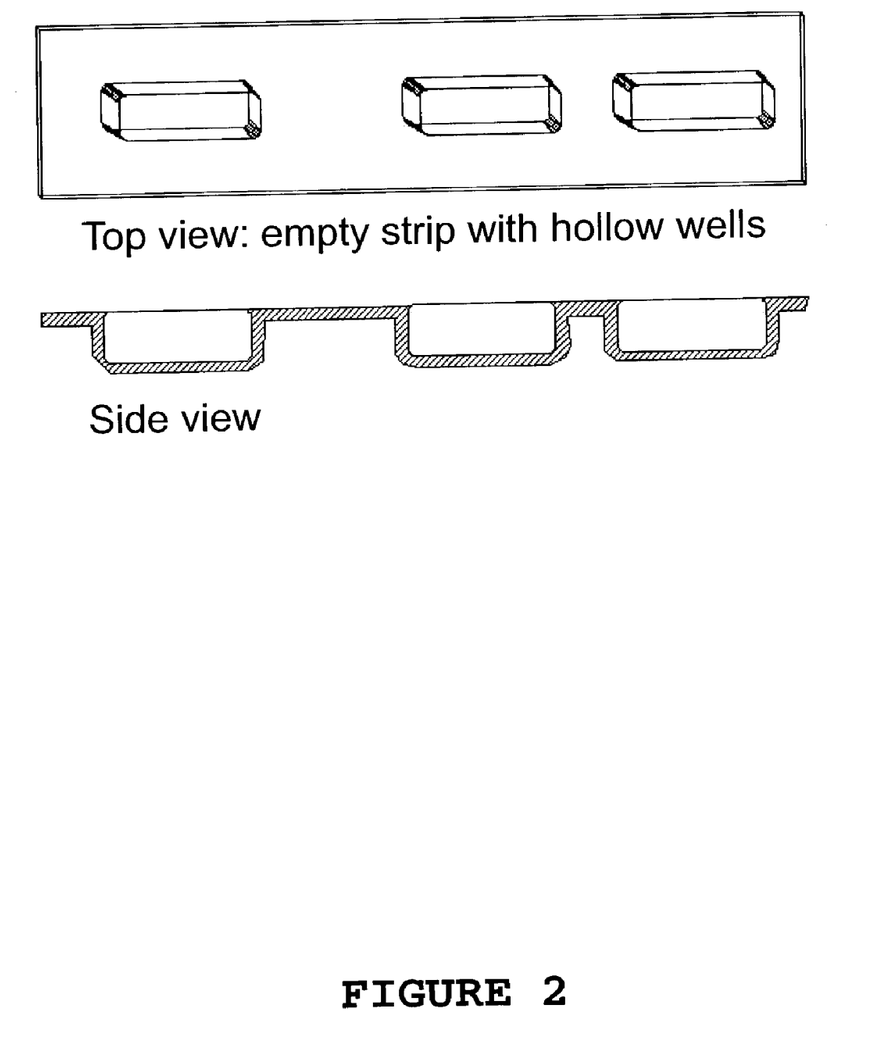
FIG. 2 is a schematic representation of a three-well blister pack employed in the exemplified embodiments described below.

The typical thickness of the thermoformable film was 0.010 inches (10 mils) or 250 µm. If better casting definition is required, a 5 mils film can be used. The test form design for the blister pack (BP) is shown in FIG. 2. The mold was designed to be placed in its entirety in a temperature controlled oven and allowed to reach thermal equilibrium at the desired thermoforming temperature. Either pressure and/or vacuum forming of the film was employed. The thermoforming temperature of the film was typically 100° C. and 125° C. for the PETG BP and the COC containing BP, respectively.

In addition to the thermoformable, plastic packaging materials described above, the use of other packaging materials that are malleable at temperatures preferably ranging from 10° C. and above are also within the scope of the instant invention. Typically, the malleable packaging materials are reflective to incident infrared and microwave radiation. The packaging materials of most interest are those which are malleable and can be shaped by compressive die casting methods. One such substance is aluminum and commercial alloys thereof. The source of an aluminum film used in the examples provided hereinbelow was HEFTY® cake pans produced by Pacivity Corporation (Lake Forest, Ill.). The material was 5 mils thick and could be easily cut into suitable strips and formed by compressive manipulation into the blister pack configuration of FIG. 2.

The in situ drying of the films to be individually cast within the well(s) of the test BP was conducted by means of two types of electromagnetic (radiant) energy—infrared (IR; wavelength between 740 nanometers and 1.0 mm and frequency between $4 \times 10^{14}$ Hz and $3 \times 10^{11}$ Hz) and microwave (MW; wavelength between 1.0 mm and 1.0 m and frequency between $3 \times 10^{11}$ Hz and $3 \times 10^{8}$ Hz)

In the case of IR radiation, the BP containing the test sample was exposed to incident radiant energy initiated thermal excitation in a small drying tunnel. The inlet air to the drying region was typically ambient but could be preheated. It will be appreciated by those skilled in the art that a vast combination of incident radiant intensities, pneumatic flow rates and inlet air temperatures can be employed to achieve the desired drying conditions of the instant invention. Moreover, a skilled artisan would further appreciate that the air inlet temperature can be an important contributor to both the overall transfer of thermal energy to the substrate and the removal of evaporated or volatilized material. A typical drying setup used in the examples provided hereinbelow is described as follows. The superficial linear velocity of ambient air flow over the sample BP was 80 ft/minute. The IR source delivered 10 watts/in$^2$ at the BP interface in an IR wavelength range of 2 to 10 μm with a peak intensity of about 3 μm.

Microwave drying is extremely efficient for water removal but requires that considerable control be exercised to prevent thin film distortion as drying progresses. Particular care must be taken for water soluble polymers such as oligosaccharides and other highly hydroxyl substituted hydrocolloids to avoid unwanted film distortions. Typically, microwave drying for this application is used in combination with conductive and/or forced air drying. With regard to the in situ evaporation of water or other microwave receptive substances, microwave drying can be a powerful method for drying or solidification, provided that, the container film is relatively invisible to the microwave energy wavelength employed. In the following examples, the drying device employed was a commercially available microwave drying apparatus (model AVC-80®) manufactured by CEM® (Matthews, N.C.) although other microwave drying devices would be suitable. The equipment was rated at 630 watts irradiating a 2000 in$^3$ chamber at a microwave frequency of 2450 MHz. The device could be attenuated from 1-100% of the rated, theoretical output by regulating on/off cycle time, and the overall exposure time controlled and recorded. Excess unused microwave energy is removed to avoid microwave density accumulation within the drying cavity for samples with small energy demand. Programming from high energy to low energy operating levels was employed as the drying progressed to avoid or minimize overheating and distortion of the films.

Plasticizer substances can be added to the film-forming composition in order to improve the physical properties of the resultant dose form. A robust dose form is desired, but one that is not brittle or easily fragmented. Plasticizers are used to preserve film flexibility which is a desired property for sublingual applications. These substances include, but are not limited to: polyols, glycerin, erythritol, sorbitol, mannitol, propylene glycol, polyglycerols, short chain aliphatic monoglycerol esters, and polyethylene oxides. Three plasticizer substances (monoacetin, glycerin, and erythritol) have been employed in the provided examples. Monoacetin or mono-glyceryl acetate is a water miscible liquid useful as a plasticizer in films. Glycerin and erythritol are examples of three and four carbon polyols, respectively, employable as film plasticizers. It will be appreciated by those skilled in the art that numerous substances can be employed as plasticizers or film modifiers depending on their chemical and physical compatibility with other constituents of the dose form and its final physical properties.

Three solvents (water, ethanol and isopropanol) were employed as representative substances for practice of the invention. Again it will be appreciated by those skilled in the art that there are a vast number of solvents with virtually an unlimited number of combinations that may be appropriate for practice of the invention. Typically, a solvent possessing a low boiling point of about 40° to 150° C., more preferably about 90° to 110° C., even more preferably about 100° C. at ambient atmospheric pressure is desired. In general, the selected solvent will exhibit a significant partial pressure at a moderate temperature range of about 40° to 80° C. Significant evaporation rates at low temperatures are desired as many drug activities are thermally sensitive and some packaging matrices have temperature limitations. Furthermore, it is important to select a volatile continuous phase which can directly interact with the incident radiant energy source selected. Wavelengths of the incident radiation can be selected to maximize energy transfer to the volatile, solvent phase while minimizing or even eliminating direct radiant transfer to the packaging matrix. Water is a particularly appropriate medium for the continuous phase as it readily undergoes infrared and microwave excitation at selected wavelength regions of the electromagnetic energy spectrum. Likewise, polar liquids such as low molecular weight alcohols are effective.

Release agents are frequently employed in film casting to assist in the removal or release of the film from the supporting surface. However, release agents are not always needed as many films are capable of spontaneously releasing from the support surface or blister pack cavity. Commonly used release agents are lipids or surfactant substances including, but limited to: lecithins, alkali salts of aliphatic organic acids (such as sodium stearate and potassium stearate), and acyl triglycerides. For practice of the present invention, two release agents were selected with two different methods of application. The first release agent, PAM® (International Home Foods, Inc., Parsippany, N.J.), is an edible, proprietary mixture of lipids and lecithin useful as an "antistick agent" in cooking. PAM® can be applied by means of a cotton swab or other means to the individual wells of the blister pack prior to filling with the film forming solution. The second release agent is potassium stearate which is a water soluble salt of a C18 fatty acid. Potassium stearate is typically incorporated into the film forming solution directly.

In addition to the above components, a variety of pharmaceutically acceptable additives may be incorporated into the film-forming composition. These pharmaceutically acceptable additives include, but are not limited to: i) flavoring agents such as citric acid, menthol, tartaric acid, and the like to season the film; ii) colorants such as tar pigments, natural colors, and the like to enhance visualization of the film; and iii) preservatives such as antioxidants and the like to maintain stability. Another class of desirable agent is that of penetration enhancers which accelerate diffusion of substances across cellular interfaces by influencing cellular membrane permeability. An example of such a penetration enhancer is dimethyl sulfoxide. Other substances of this type are, but not limited to: amides and amines such as dimethylacetamide and dimethylforamide, respectively; esters such as ethyl acetate; fatty acids such as oleic acid; and pyrrolidones such as 1-methyl-2-pyrrolidone.

The present invention is adaptable for the construction of multi-layered unit dose forms, where there is an advantage to be gained by having two or more layers of the same or different film matrices constitute the dose form. For example, it may be desirable to have one layer consist of a fast dissolving substance which contains the drug of interest to be placed against the target tissue with a second outer layer composed of a material with slow or little dissolution by the saliva and which acts as a protective coating for the inner layer. Another possible scenario would be to have one layer release the drug of interest rapidly and another layer release it slowly so as to provide the patient with immediate and sustained drug delivery into the target oral region. The ability to easily construct a layered dose form allows for a great deal of flexibility in drug delivery.

In the examples below, all solution compositions are reported on an anhydrous, nonvolatile substance basis unless otherwise indicated. Where appropriate, corrections for nonvolatile matter (adsorbed moisture) were taken into account during solution make up. For example oligosaccharide materials on a received "as is" basis can range from a few percent moisture to 12%. The confirmation of the nonvolatile solids (NVS) content of all solutions, which is given as a weight percentage, was verified by drying to constant weight at 105° C. Typically, all casting solutions were vacuum degassed prior to use. Any small evaporative loss in the degassing was corrected by compensative addition of the volatile phase. Recovered solids are reported as percent of theoretical as calculated by dividing the recovered weight by the computed, anhydrous NVS weight in the casting solution aliquot and multiplying by 100.

The following Examples are provided to describe the invention in further detail. The Examples are provided for illustratative purposes only and are not intended to limit the invention.

EXAMPLE 1

Starch Film (IR) PP/COC/PP

Instant Pure-Cote® B792 is a proprietary, cold water dispersible, modified starch manufactured by Grain Processing Corporation, Muscatine, Iowa. The PP/COC/PP film (Topas®) was used as the dose form platform with PAM® as the release agent. The aqueous casting solution contained 20% B792 and 5% w/w glycerin as a plasticizer. After 24 hours at 105° C., the loss on drying (LOD) of the casting solution was determined and indicated a nonvolatile solids (NVS) of 24.93% which is in good agreement with the 25.0% target make up. The total solution mass to be dried was 0.1745 g divided equally into the three blister pack wells of FIG. 2. After 65 minutes in the IR drying tunnel the net remaining weight was 111% of the theoretical NVS. The oval shaped dose forms released well from the molding cavity. The doses were transparent and averaged 7-9 mils thick. While exhibiting some flexibility, they could be broken by severe bending indicating that more plasticizer and perhaps a thinner film would be beneficial if a high degree of flexibility is desired. A repeat experiment in which a thermistor was introduced into one of the wells indicated the temperature of the fluid in the early stages of the drying cycle was approximately 80° C. There was no indication of delamination or destruction of the dose form film platform.

EXAMPLE 2

Carboxymethyl Cellulose Film (IR) PP/COC/PP

A food-grade, low viscosity (45 centipoise for a 2.0% w/w solution as measured with a Brookfield RV viscometer employing spindle #1) sodium carboxymethyl cellulose (CMC) was used to prepare an aqueous 5.0% w/w total NVS solution containing 4.0% CMC and 1% erythritol. The total solution to be dried (0.7083 g) was divided equally over the three wells of the test BP strip. After 45 minutes exposure in the IR drying tunnel the final net weight was 105% of the theoretical NVS yielding three dose form films averaging 13 mg each. The film patches were clear and flexible and released readily from the BP film mold platform.

EXAMPLE 3

Pullulan Film (IR) PP/COC/PP

Pullulan is a linear glucan consisting of repeating maltotriose units linked by α-D-(1-6) linkages. It forms low viscosity solutions in the 10% to 20% range. The pullulan used, PF-20, was obtained from Hayashibara Co. LTD., Japan. The polymer forms clear films with high tensile strength and both dries and rehydrates rapidly. Two aqueous pullulan solutions each with different plasticizers were prepared at a total NVS of 16.5% w/w containing 20% of the total NVS as plasticizer. The plasticizers used were monoacetin and erythritol. The sample BP strip was loaded with 500 to 600 mg of solution divided equally between the three wells and dried in the IR drying tunnel. After 45 minutes the monoacetin and erythritol plasticized films had dried to 110% and 105% of their theoretical NVS content, respectively. The erythritol containing film was clear and the monoacetin film was white and opaque. Both films released easily and were moderately flexible. Each film had a net weight of approximately 30 mg.

EXAMPLE 4

Hydroxypropyl Methyl Cellulose Film (IR) PP/COC/PP

A low viscosity hydroxypropyl methyl cellulose (HPMC) type E05 was obtained from Dow Chemical Company, Midland, Mich. HPMC is a good film former similar to CMC as both are substituted β-1-4 glucans (cellulose). In contrast to CMC, which bears an anionically charged substituent on the polymer backbone, HPMC is comprised of a combination of non-ionic substituents. An aqueous casting solution was prepared at a total NVS concentration of 18.1% comprised of 20% erythritol and 80% HPMC. The total weight of the casting solution was 769 mg divided equally between the three wells of the test BP strip. After 45 minutes in the IR drying tunnel, the net dried weight was 108% of the theoretical NVS. The film swatches were clear and released spontaneously without the use of a release agent. The weight of each film swatch was approximately 50 mg.

EXAMPLE 5

Gum Arabic Film (IR) PP/COC/PP

Gum arabic is a highly branched polysaccharide derived as an exudate from the acacia tree. As a film former it is characterized by very low viscosity even at high concentrations. For example a 40% w/w solution is readily transferred by simply pouring from one container to another. The material used for this example was a refined, spray dried gum arabic (FT Pre-Hydrated®) obtained from TIC Gums Inc., Belcamp, Md. A 35.0% total NVS aqueous casting solution was prepared using 20% erythritol and 80% gum arabic based on the total NVS content. The total weight of the casting solution was 966 mg evenly divided between the three wells of the test BP strip. After drying for 90 minutes in the IR drying tunnel the final net weight was 110% of the theoretical NVS. The film swatches spontaneously released from the casting well without using a release agent. The film swatches averaged 125 mg each and were clear and amber colored. Although the swatches had good film definition, they were relatively brittle indicating the need for a higher concentration of erythritol or perhaps a different plasticizer.

EXAMPLE 6

Sodium Alginate Film (IR) PP/COC/PP

Sodium alginate is a sodium salt of alginic acid, a polysaccharide isolated from seaweed or kelp. Under appropriate conditions it forms insoluble gels and is an excellent film former. The product employed in this example, Manucol® LB, was obtained from ISP Alginates, San Diego, Calif. Manucol® LB is a low viscosity form of sodium alginate. An aqueous casting solution was prepared containing 5.75% total NVS which consisted of 70% Manucol LB and 30% glycerin. The total weight of the casting solution distributed over the three wells of the BP test strip was 689 mg. After drying for 30 minutes in the IR drying tunnel, the final net weight was 104% of the theoretical NVS. No release agent was required. The resulting films were very clear and flexible and averaged 13 mg.

The preceding examples utilized water soluble, polysaccharides. The next set of examples describe the preparation of protein based films.

EXAMPLE 7

Sodium Caseinate Film (IR) PP/COC/PP

The sodium caseinate employed in this example, type NA94, was manufactured by Molkereigselschaft Lauingen mb, Germany. An aqueous 12.6% NVS solution was prepared and the NVS content was composed of 70% sodium caseinate and 30% glycerin. The total weight of the casting solution was 448 mg and was equally distributed over the three wells of the sample BP strip. After drying for 36 minutes in the IR drying tunnel, the final net weight was 100% of the theoretical NVS. Release of the film was assisted by employing the release agent PAM®. The recovered film swatches were clear, flexible and physically undistorted. Each film swatch averaged 19 mg.

EXAMPLE 8

Soy Protein Isolate Film (IR) PP/COC/PP

Soy protein isolate, type SL, was obtained from Cargill Incorporated, Wayzata, Minn. An aqueous 12.6% NVS solution was prepared and the NVS content was composed of 70% soy protein isolate and 30% glycerin. The total weight of the casting solution (524 mg) was equally distributed over the three wells of the test BP strip. After drying for 32 minutes in the IR drying tunnel, the net weight recovered was 117% of the theoretical NVS. The film swatches were clear and flexible. With a higher degree of drying to 111% of theoretical NVS, the resultant films readily curled. Employing a greater percentage of glycerin or perhaps a different plasticizer should alleviate this unwanted curling. No release agent was required.

EXAMPLE 9

Zein Film (IR) PP/COC/PP

Purified zein from corn was obtained from the Sigma-Aldrich Company, St. Louis, Mo. Zein is not soluble in water at nominal pH levels (pH 4-8), but is soluble in short chain alcohol hydrates. Typically, 70% w/w alcohol in water is utilized. Two solvents were used to prepare an 18.7% NVS solution in which the NVS content was composed of 70% zein and 30% glycerin. The solvents employed were a 70/30% isopropyl alcohol (IPA)/water solution and a 70/30% ethyl alcohol (EA)/water solution. The total weight of the casting solutions were 154 mg and 183 mg for the IPA/water solution and the EA/water solution, respectively. The casting solutions were equally distributed over the three wells of each sample BP strip. The drying in the IR drying tunnel was rapid and yielded a 106% recovery of the theoretical NVS for the IPA solvent in 28 minutes and a 111% recovery of the theoretical NVS for the EA solvent in 25 minutes. Both films were clear, light yellow in color and very flexible. Release was excellent using PAM®. Both types of film swatches averaged 10 mg.

The following series of examples describe double-layered film constructs formed in situ.

EXAMPLE 10

Zein/Sodium Alginate Double Film (IR) PP/COC/PP

A first film was cast using a 18.7% total NVS solution of zein in 70% IPA wherein the NVS was composed of 70% zein and 30% glycerin. The total weight of the casting solution (276 mg) was divided equally among the three wells of the sample BP strip. After drying for 55 minutes in the IR drying tunnel, the net weight recovered was 117% of the theoretical NVS or about 20 mg per film swatch. The resulting films were clear and light yellow. A second casting solution of aqueous sodium alginate was prepared at 5.75% total NVS and the NVS was composed of 70% sodium alginate and 30% glycerin. The second casting solution also contained 0.002% w/w of the food dye Blue #1. The total weight of the second casting solution was 570 mg and it was divided equally into each of the three wells on top of the dried zein film. After 40 minutes of drying in the IR drying tunnel, the net solids recovered were essentially 100% of the theoretical NVS. The resulting film swatches were clear and displayed a light green appearance resulting from the blue film overlay on the yellow base film. Careful examination showed regions of more yellow hue associated with the zein base film at the edges. Notably, there was no readily apparent line of demarcation between the two different films in the middle of the dose form. The dose forms easily released without the use of a release agent and were quite flexible. Each film swatch was approximately 50 mg.

EXAMPLE 11

Pullulan/Sodium Alginate Double Film (IR) PP/COC/PP

A first film was cast using a 17.3% total NVS acidic, aqueous solution of pullulan wherein the composition of the solution solids was 75% pullulan, 20% erythritol and 5% citric acid. The solution also contained 0.05% of the food colorant Red #3. The total weight of the casting solution (654 mg) was distributed equally over the three wells of the sample BP strip. After 46 minutes in the IR drying tunnel, the recovered solids were 111% of the theoretical NVS. The film swatches were pink and clear. The second casting solution consisted of 5.3% total NVS in an aqueous solution wherein the NVS was composed of 80% sodium alginate and 20% erythritol. The second casting solution also contained 0.002% Blue #1. The total weight of the second casting solution was 598 mg and it was equally layered over the prior cast film in each of the three wells. After 55 minutes drying in the IR drying tunnel, the weights of the recovered solids were 112% of the theoretical NVS. The resulting film swatches were purple with an occasional blue hue at the edge resulting from the top film overlapping the bottom film. The films were flexible and released easily without the need for a release agent. Each recovered film swatch averaged 50 mg.

EXAMPLE 12

Pullulan/CMC Double Film (IR) PP/COC/PP

A first film was cast using a 16.5% total NVS aqueous solution of pullulan with an NVS composition of 80% pullulan and 20% erythritol. The solution also contained 0.002% Blue #1. The total weight of the casting solution was 635 mg and was distributed equally over the three wells of the sample BP strip. After 40 minutes in the IR drying tunnel, the weight of the recovered solids was 92% of the theoretical NVS. The film within the well was clear and light blue. The second aqueous casting solution was 5.0% total NVS wherein the NVS was comprised of 80% CMC and 20% erythritol. The total weight of the second casting solution was 748 mg and it was evenly divided among the three wells and cast on top of the previously dried first film. After 55 minutes in the IR drying tunnel, the weights of the recovered solids were 111% of the theoretical NVS. The resulting film swatches were purple with occasional blue hued edges as seen in Example 11. The dose-forms were clear and flexible and easily released from the casting well. Each recovered film swatch averaged 50 mg.

In the next set of examples, a microwave chamber was utilized in place of the infrared drying tunnel in order to remove the volatile solvents.

EXAMPLE 13

Pullalan Film (MW) PP/COC/PP

The microwave (MW) drying chamber described earlier was employed to evaporate the solvent from the casting solution. A 16.5% total NVS aqueous solution of pullulan was employed in which the NVS content was 80% pullulan and 20% erythritol. The total weight of the casting solution was 364 mg and it was equally divided into the three wells of the sample BP strip. PAM® was utilized as a release agent. The initial microwave chamber power setting was 25% and the exposure time intervals were 5 minutes. At the end of each interval the film strip was examined and the net weight recorded. At the end of 30 minutes, the net recovered weight was 145% of the theoretical NVS. Subsequently, the power was reduced to 10% while maintaining the 5 minute exposure intervals. At a cumulative time of 50 minutes, the net weight of the recovered solids was 106% of the theoretical NVS. The resulting films were clear and flexible. The average weight was 21 mg.

EXAMPLE 14

Sodium Alginate Film (MW) PP/COC/PP

A 5.3% total NVS aqueous solution of sodium alginate was prepared wherein the NVS was composed of 80% sodium alginate and 20% erythritol. PAM® was used as a release agent. The total weight of the casting solution was 323 mg and was divided equally between the three wells of the sample BP strip. Initially, the microwave chamber power setting was set at 50% and the exposure interval set at 5 minutes. After just 2 minutes, the recovered solids were 106% of theoretical, but the films were distorted from rapid and excessive heat accumulation. The next trial involved reducing the power to 10% but maintaining the 5 minute exposure interval. The total weight of the casting solution was increased to 479 mg. After 25 minutes, the net weight of the solids recovered was 312% of theoretical NVS indicating a relatively slow drying rate. Therefore, the power setting was increased to 20%. After an additional 3 minutes at 20% power, the recovered solid weight had decreased to 117% theoretical NVS. The films were clear and released readily. The average weight of a film swatch was 10 mg.

The next set two examples describe dose forms made according to this invention in which active drugs are present. One example uses a high active dose (mg range), and the other a very low active dose (µg range).

EXAMPLE 15

Caffeine Film (IR) PP/COC/PP

An aqueous casting solution was prepared containing 8.0% pullulan, 2.0% erythritol and 2.0% caffeine. The total weight of the casting solution used was 1.23959 which was equally divided between the three wells of the sample BP strip. After 90 minutes in the IR drying tunnel the recovered solids were 109% of the theoretical NVS. The films were white and opaque. The film swatches were capable of being removed intact from the casting well, but use of a release agent is indicated. The recovered film swatches were very flexible. Each swatch had an average weight of 45 mg and contained 8.3 mg of caffeine.

EXAMPLE 16

Scopolamine Film (IR) PP/COC/PP

A casting solution was prepared containing 4.0% CMC and 1.0% erythritol. A 10.0 mg aliquot of scopolamine HCl was dissolved into 50 g of the casting solution thereby yielding a scopolamine HCl concentration of 200 µg/g of the casting solution. A 1.2543 g amount of the casting solution containing the drug was equally divided between the three wells of the sample BP strip. PAM® was employed as a release agent. After 45 minutes in the IR drying tunnel the recovered weight was 105% of the theoretical NVS. The resulting films easily released from the casting well and were clear and flexible. Each film swatch averaged 22 mg and contained 8.4 µg of scopolamine HCl.

The following set of examples utilize the PETG film matrix, EASTAR®, in place of the PP/COC/PP film Topas® used in the previous examples.

EXAMPLE 17

Pullulan Film (IR) PETG

An aqueous casting solution was prepared containing 8.0% pullulan and 2.0% erythritol. A 0.6754 g aliquot of the solution was divided equally between the three wells of the sample PETG BP strip. PAM® was employed as a release agent. After 40 minutes in the IR drying tunnel the recovered weight was 103% of the theoretical NVS. The films, which released easily from the casting well, were clear and flexible. There was no indication of destruction or distortion of the blister pack matrix on visual examination.

EXAMPLE 18

CMC Film (IR) PETG

An aqueous casting solution was prepared containing 4.0% CMC and 1.0% erythritol. The same BP sample casting strip employed in Example 17 was used in this example. A 0.7613 g aliquot of the solution was divided equally between the three wells of the sample BP strip. No further release agent was used other than that carried over from the prior example. After 30 minutes in the IR drying tunnel the recovered weight was 107% of the theoretical NVS. The films released easily from the casting well and were clear and flexible. There was no visible destruction or distortion of the blister pack matrix even after two drying cycles.

EXAMPLE 19

Pullulan Film (MW) PETG

An aqueous casting solution was prepared containing 8.0% pullulan and 2.0% erythritol. A 0.7603 g aliquot of the casting solution was equally divided between the three wells of the sample BP strip. A new PETG sample strip was used and PAM® was employed as the release agent. The power level selected was 25% of maximum power (heat cycle modulation) for the CEM® microwave drier. The blister packs were weighed after each consecutive 5 minute drying interval to track convergence of drying to the theoretical NVS weight and allow for adjustments in the power level if there was an indication of film or BP matrix distortion. After two 5 minute drying cycles and a 58% weight loss, a visual inspection of the BP sample strip indicated a minor distortion of the BP base at the center in two of the wells. The MW power was reduced to 10% of maximum and the 5 minute cycles were continued three times while examining the BP sample strip and contents each time. No further distortion occurred at this radiant power level and this radiant exposure level was employed for the rest of the test. The drying was discontinued at 75 minutes total microwave exposure from the beginning of the test. The recovered weight was 115% of the theoretical NVS. The films were clear, flexible and released readily from the casting wells.

A second test was conducted at the optimal 10% power level indicated above using a new PETG BP sample strip. Each cycle interval was 15 minutes and the weights were tracked for convergence to the theoretical NVS as well as to examine the BP assembly for either film or base matrix distortion. A 0.7592g aliquot of the casting solution described above was equally divided between the three wells of a new sample BP strip. PAM® was employed as the release agent. After 75 minutes the recovered solids were 111% of the theoretical NVS. The films were clear, released easily from the casting wells and there was no distortion of either film or BP matrix by visual examination.

EXAMPLE 20

CMC (MW) PETG

An aqueous casting solution was prepared containing 4.0% CMC and 1.0% erythritol. A 1.1842 g aliquot was equally divided between the three casting wells of the sample BP strip. The initial power level employed was 10% using a 15 minute interval between weighings. After 15 minutes (first cycle) a minor distortion was observed in 2 of the three wells near the center. The power was reduced to 5% and the 15 minute interval maintained for the rest of the drying test. No further distortion was observed for the films or the BP support matrix. After 105 minutes total microwave exposure, the recovered solids were 115% of the theoretical NVS. The resulting films were clear, flexible and undistorted except for the small region in the center of the two initial wells which experienced minor heat distortion in the first cycle.

The following three examples utilize a malleable aluminum film matrix in place of the thermoformable plastic film matrices used in the previous examples.

EXAMPLE 21

Pullulan (IR) Aluminum BP

An aqueous casting solution comprising 8.0% pullulan and 2.0% erythritol was prepared. A 0.4986 g aliquot was equally divided between the three casting wells of the sample aluminum BP strip. After 53 minutes in the IR drying tunnel the recovered weight was 113% of the theoretical NVS. The resulting films were clear, flexible and easily removed from the casting cavity of the blister pack.

Aluminum is a good heat conductor and constitutes a majority of the mass and surface area of the test BP strip shown in FIG. 2. Because of the possibility that the drying rate was artifactually reduced by heat loss from the well contents to the contiguous blister pack matrix and ultimately to the forced air stream within the drying tunnel, a second test was conducted with no forced air flow. A 0.5199 g aliquot of the aqueous casting solution described above was equally divided between the three casting wells of the sample BP strip. The forced air was turned off on the IR drying tunnel. After 25 minutes the recovered solids were 110% of the theoretical NVS, indicating that the drying rate was significantly influenced by thermal loss to the forced air component of the drying tunnel. In practice, thermal loss can be reduced by heating the forced air component as well as by appropriately designing the drying tunnel configuration to expand the exposed surface area relative to the volumetric displacement rate above it. The recovered films displayed identical properties to those of the prior test which employed forced air displacement in the IR drying tunnel.

EXAMPLE 22

CMC (IR) Aluminum BP

An aqueous casting solution comprising 4.0% CMC and 1.0% ET was prepared. A 0.5216 g aliquot was equally divided between the three casting wells of the sample BP strip. The standard IR drying tunnel conditions were employed including forced ambient air over the sample blister pack strip. After 30 minutes in the IR drying tunnel the recovered solids were 107% of the theoretical NVS. The recovered films were clear, flexible and easily released from the casting well.

EXAMPLE 23

Pullulan (MW) Aluminum BP

An aqueous casting solution comprising 8.0% pullulan and 2.0% ET was prepared. A 0.7611 g aliquot was equally divided between the three casting wells of the sample BP strip. The MW power was 100% of the CEM rated output and the initial weighing interval moved from 10 minutes to 15 minutes as the test progressed. The high radiant exposure level relative to that of the thermoformed BP matrix carriers described hereinabove is due to the opaque, reflective nature of the aluminum BP matrix. The BP matrix is centrally located within the microwave chamber thereby restricting incident radiant exposure to only that emanating from the topside region. In practice, the microwave cavity accepting the blister pack film web would be geometrically designed to reduce underside and lateral incident radiant microwave energy excursion and thereby improve incident delivery to the target surface area. After 50 minutes the recovered solids were 114% of the theoretical NVS. The recovered films were clear, flexible and easily released from the casting well.

The following set of examples utilize a microemulsion and micelle containing film-forming matrix. Basically two types of dispersed phase liquids are found in the art of encasement or encapsulation. Microemulsions, which typically scatter light in solution, are typically under 1 micron but can have populations of several microns. Micelles are essentially discrete molecular ensembles in the nanometer range and are usually so small that, in solution, they do not scatter light.

EXAMPLE 24

Microemulsion Film (IR) PP/COC/PP

A homogeneous mesophasic solution containing vitamin A palmitate and vitamin D3 which spontaneously forms an emulsion when mixed with an aqueous medium was prepared. The solution contained 4.75% vitamin A palmitate at 1.7 million IU/g (BASF Corp., Parsippany, N.J.), 0.05% vitamin D3 crystals at 40 million IU/$_g$ (Duphar Ltd., Copenhagen, Denmark), and 26.55% polysorbate 80 (Sigma Chemical Company, St. Louis, Mo.) with the remainder being water. This solution has 80,000 IU/g vitamin A and 20,000 IU/g vitamin D3 with a total NVS content of 31.4%. A 2.59 aliquot of the above solution was incorporated into 47.59 of a 10.0% pullulan solution and homogenized employing a hand held rotor-stator homogenizer at 10,000 rpm (Omni International, Gainesville, Va.). The resulting slightly opalescent solution contained 4,000 IU/g vitamin A and 1,000 IU/g vitamin D and had a NVS content of 11.1%. Examination by light microscopy indicated no significant amount of colloidal lipid material at a resolution of 0.5 microns. A 0.7569 g aliquot of the above casting solution was equally divided between the three wells of the test blister strip. After 40 minutes in the IR drying tunnel the recovered weight was 109% of the theoretical NVS. The films, slightly distorted indicating uneven drying, were slightly cloudy but largely transparent, flexible and readily released from the casting well. There was no evidence of lipid accumulation or pooling on the surface indicating that the emulsion was encapsulated within the film. Each film swatch contained on the average 1,000 IU of vitamin A and 250 IU of vitamin D, representing 20% and 60%, respectively, of the recommended daily intake (RDI) established by the U.S. Food and Drug Administration.

EXAMPLE 25

Micellar Film (IR) PP/COC/PP

A 5.0% micelle containing mesophasic solution of β-carotene (a highly insoluble, lipophilic, dietary source of vitamin A) was prepared by dissolving β-carotene crystals (Sigma Chemical Co., St Louis, Mo.) into a 50/50 blend of PEG-40 hydrogenated caster oil (BASF Corp., Mount Olive, N.J.) and medium chain triglycerides (NEOBEE 1053, Stepan Co., Maywood, N.J.) at 320° F. to form a eutectic melt. The eutectic melt was immediately quenched by addition to an equivalent weight of water. The resulting deep red solution which exhibited a syrup-like consistency undergoes spontaneous micelle formation upon further dilution into an aqueous medium. A pullulan casting solution was prepared by addition of 1.0 g of the 5.0% β-carotene mesophase mixture to 99.0 g of a 10.0% pullulan solution. The theoretical NVS was 10.0%. A 0.7514 g aliquot of the casting solution was equally divided between the three wells of the test blister strip. After 47 minutes in the IR drying tunnel the recovered solids were 104% of the theoretical NVS. The resulting orange films were clear, flexible and easily released from the casting well. Each film on the average contained 125 μg of β-carotene or 200 IU of vitamin A. One of the three films was suspended into 20 ml of water and rapidly dissolved with swirling to form a clear, yellow solution.

While certain embodiments of the present invention have been described and specifically exemplified above, various other embodiments will be apparent to those skilled in the art from the foregoing disclosure. The present invention is, therefore, not limited to the particular embodiments described, but is capable of considerable variation and modification without departure from the scope and spirit thereof as set forth in the following claims.

What is claimed is:

1. A method for the concomitant formation and packaging of a dosage unit of at least one systemically active pharmaceutical agent as an orally administrable, solid, said method comprising:
   a. providing a sheet of packaging material having at least one depression therein said packaging material comprising at least a thermoformable plastic;
   b. providing a flowable composition comprising said at least one pharmaceutical agent, at least one pharmaceutically acceptable non-volatile material which comprises a film-forming substance and a volatile liquid carrier medium in which the pharmaceutical agent(s) and non-volatile material are dissolved or dispersed;
   c. depositing said composition in said at least one depression;
   d. subjecting said deposited composition to radiant energy, comprising at least infrared energy, said radiant energy being effective to volatilize said liquid carrier medium, thereby forming said dosage unit as a solid film matrix comprising said non-volatile material, said film matrix including said at least one pharmaceutical agent, the radiant energy being selected to effect preferential absorption by the deposited composition without compromising the packaging material; and
   e. affixing a lidding sheet to said sheet of packaging material to seal said solid dosage unit within said depression thereby producing a packaged dosage unit of said at least one pharmaceutical agent.

2. The method of claim 1, wherein steps b, c and d are each repeated at least once to provide a multi-layer solid dosage unit.

3. The method of claim 2, wherein in at least one repetition of step b, a pharmaceutically active agent is used which is different from the pharmaceutically active agent used in a prior execution of step b.

4. The method of claim 2, wherein in at least one repetition of step b, a non-volatile material is used which is different from the non-volatile material used in a prior execution of step b.

5. The method of claim 1, wherein said lidding sheet is reptureable.

6. The method of claim 1, wherein said lidding sheet is peelable.

7. The method of claim 1, wherein the radiant energy employed in step d is infrared energy with a wavelength between 740 nanometers and 1.0 millimeter ($4 \times 10^{14}$ Hertz to $3 \times 10^{11}$ Hertz, respectively).

8. The method of claim 1, wherein the radiant energy employed in step d is a combination of microwave energy and infrared energy.

9. The method of claim 8, wherein the combination of microwave energy and infrared energy is applied simultaneously.

10. The method of claim 8, wherein the combination of microwave energy and infrared energy is applied sequentially.

11. The method of claim 1, wherein said depression(s) have an inside configuration with a transverse cross-section in the shape of a closed curve, a polygon or a fragment thereof.

12. The method of claim 1, wherein said depression(s) have an inside configuration with a longitudinal cross-section shaped such that said dosage unit conforms to a predetermined surface in the oral cavity.

13. The method of claim 12, wherein said surface is the anterior sublingual platform.

14. The method of claim 12, wherein said surface is the anterior sublingual ceiling formed by the base of the tongue.

15. The method of claim 8, wherein the microwave energy has a wavelength between 1.0 millimeter and 1.0 meter ($3\times10^{11}$ Hertz and $3\times10^{8}$ Hertz, respectively).

16. The method of claim 1, wherein said sheet of packaging material is a composite of a thermoformable plastic and a malleable metal.

17. The method of claim 16, wherein the malleable metal is aluminum or an aluminum alloy.

\* \* \* \* \*